(12) United States Patent
Gonzalez

(10) Patent No.: US 10,245,379 B2
(45) Date of Patent: Apr. 2, 2019

(54) CANNULATED DOSE DELIVERY DEVICE, SYSTEM AND METHOD OF USE

(71) Applicant: Med Dose Solutions, LLC, Jackson, TN (US)

(72) Inventor: Steven M. Gonzalez, Jackson, TN (US)

(73) Assignee: Med Dose Solutions, LLC, Jackson, TN (US)

( * ) Notice: Subject to any disclaimer, the term of this patent is extended or adjusted under 35 U.S.C. 154(b) by 323 days.

(21) Appl. No.: 15/133,299

(22) Filed: Apr. 20, 2016

(65) Prior Publication Data

US 2017/0304536 A1  Oct. 26, 2017

(51) Int. Cl.
*A61M 5/178* (2006.01)
*A61M 39/10* (2006.01)

(52) U.S. Cl.
CPC ............ *A61M 5/178* (2013.01); *A61M 39/10* (2013.01); *A61M 2005/1787* (2013.01)

(58) Field of Classification Search
CPC .................. A61M 5/178; A61M 39/10; A61M 2005/1787
See application file for complete search history.

(56) References Cited

U.S. PATENT DOCUMENTS

2010/0286513 A1* 11/2010 Pollard, Jr. ........ A61M 5/31511
600/432

* cited by examiner

*Primary Examiner* — Bradley J Osinski
(74) *Attorney, Agent, or Firm* — Veritay Group, IP; Susan B. Fentress

(57) ABSTRACT

The present subject matter includes a cannulated delivery device made of an adapter configured to connect to a syringe; a delivery device tip configured to connect to a dosing chamber; an internal chamber of the cannulated delivery device connecting the adapter and to the delivery device tip, and the internal chamber defining a dose pathway and a system and method of use of the device to increase dosage delivery to a patient while maintaining a sterile fluid pathway.

18 Claims, 5 Drawing Sheets

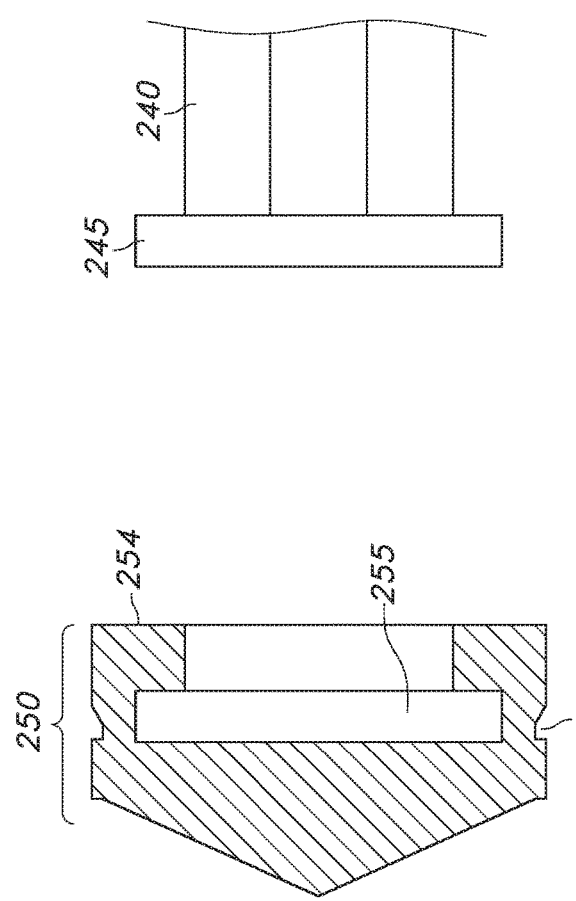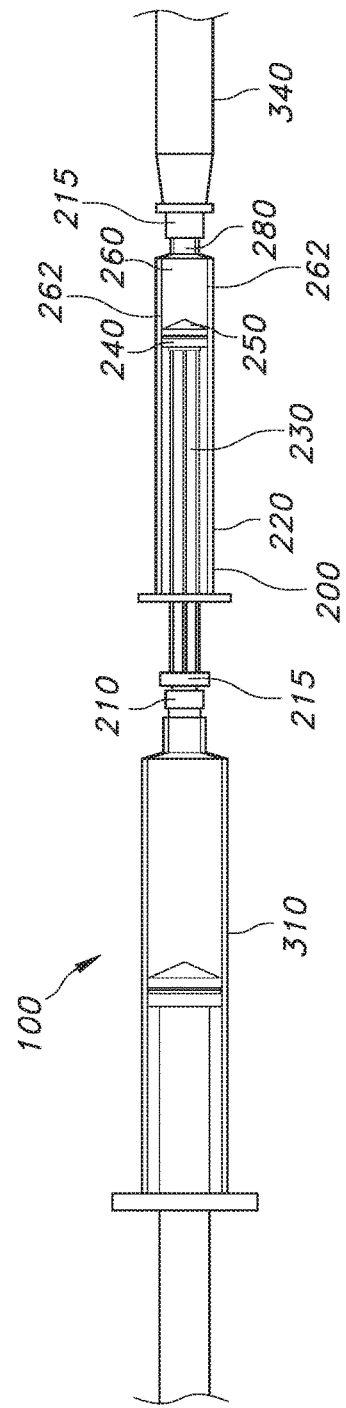

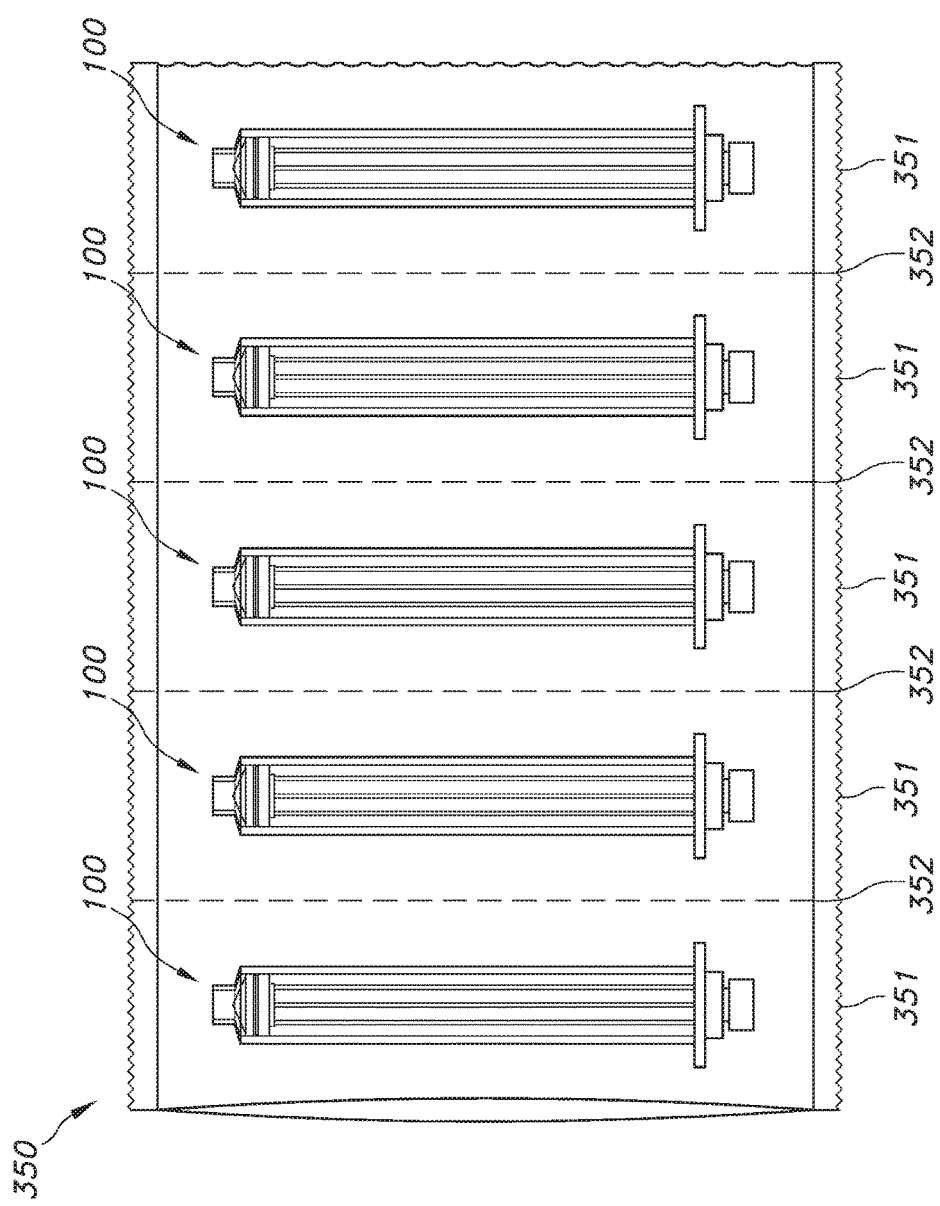

CANNULATED DOSE DELIVERY DEVICE, SYSTEM AND METHOD OF USE

CROSS REFERENCE TO RELATED APPLICATION

NONE

STATEMENT REGARDING FEDERALLY SPONSORED RESEARCH OR DEVELOPMENT

None.

REFERENCE TO SEQUENCE LISTING, A TABLE FOR A COMPUTER PROGRAM LISTING COMPACT DISC APPENDIX

None.

FIELD OF THE INVENTION

The subject of this invention is a cannulated dose delivery device that is configured to permit internal flushing of a syringe dose chamber

BACKGROUND OF THE INVENTION

In various types of medical applications, a contrast medium or radioactive agent is delivered via a dosing syringe. A dosing syringe is a simple pump made of a plunger that fits tightly in a tube. The plunger can be pulled and pushed along inside a cylindrical tube (called a barrel), allowing the syringe to take in and expel a liquid or gas through an orifice at the open end of the barrel. The open end of the syringe can be fitted with a hypodermic needle, a nozzle, or tubing to help direct the flow into and out of the barrel. In nuclear medicine, injections of various radioactive elements is necessary. By delivering a complete dose to the patient and leaving no residual or very little residual dose is very desirable for many reasons, in order to increase the accuracy of the scan, the dosing syringe, in nuclear medicine applications, is flushed to facilitate the complete delivery of the contrast agent. A need exists in the industry to provide a self-flushing dosing syringe device,

SUMMARY OF THE INVENTION

The present subject matter includes a cannulated dose delivery device. This device is made of a plunger housed in a barrel, wherein the plunger is made, of: a plunger proximal end connector configured to receive a washing agent; a plunger end cap configured to facilitate the washing of a delivery chamber of the barrel; an elongated cylinder having an internal chamber defining a fluid pathway between the plunger proximal end connector and the plunger end cap; wherein the plunger end cap is made of a plurality of slits in the distal end of the plunger end cap.

This invention further provides a cannulated dose delivery system made of a plunger housed in a barrel, wherein the plunger has a plunger proximal end connector configured to receive a washing agent; a plunger end cap configured to facilitate the washing of a delivery chamber of the barrel; an elongated cylinder having an internal chamber defining a fluid pathway between the plunger proximal end connector and the plunger end cap wherein the plunger end cap is made of a plurality of slits in the distal end of the plunger end cap; a distal connector configured to connect a cannulated dose delivery device to a delivery port: and a saline flush syringe connected to the plunger proximal end connector and a delivery port to a patient.

This invention further provides method to increase dosage delivery to a patient while maintaining a sterile fluid pathway including the steps of: providing a plunger housed in a barrel, wherein the plunger has; a plunger proximal end connector configured to receive a washing agent; a plunger end cap configured to facilitate the washing of a delivery chamber of the barrel; an elongated cylinder having an internal chamber defining a fluid pathway between the plunger proximal end connector and the plunger end cap; wherein the plunger end cap comprises a plurality of slits in the distal end of the plunger end cap; a distal connector configured to connect a cannulated dose delivery device to a delivery port and a plunger top cap; attaching a needle to the distal end attachment port; connecting a saline flush syringe to the plunger proximal end connector; connecting a delivery port to a patient; delivering a dose of the contrast agent or medication into the delivery chamber; attaching the cannulated dose delivery device distal connector is attached to a patient delivery port; removing the plunger top cap; connecting the saline flush syringe to the cannulated dose delivery device via the plunger proximal connector; and depressing the flush syringe to deliver a washing solution to the dosing chamber to facilitate flushing of a wall of the dosing chamber to increase dosage delivery to a patient.

BRIEF DESCRIPTION OF THE SEVERAL VIEWS OF THE DRAWING

The drawing shows schematically a cannulated dose delivery device and method of use according to an example form of the present invention. The invention description refers to the accompanying drawings:

FIG. 5A and 5B shows a side view of an exemplary embodiment of the plunger end cap of the exemplary embodiment of the cannulated dose delivery device system.

FIG. 6 shows an exemplary embodiment of delivery system including the cannulated dose delivery device.

FIG. 7 shows an exemplary embodiment of a plurality of cannulated dose delivery devices in a sterile package.

DETAILED DESCRIPTION OF THE INVENTION

The present invention may be understood more readily by reference to the following detailed description of the invention. It is to be understood that this invention is not limited to the specific devices, methods, conditions or parameters described herein, and that the terminology used herein is for the purpose of describing particular embodiments by way of example only and is not intended to be limiting of the claimed invention. Also, as used in the specification including the appended claims, the singular forms "a," "an" and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment.

These and other aspects, features and advantages of the invention will be understood with reference to the detailed description herein, and will be realized by means of the various elements and combinations particularly pointed out in the appended claims. It is to be understood that both the foregoing general description and the following detailed description of the invention are exemplary and explanatory of preferred embodiments of the inventions, and are not restrictive of the invention as claimed. Unless defined otherwise, all technical and scientific terms used herein have the same meaning as commonly understood by one of ordinary skill in the art to which this invention belongs.

Figure 1:
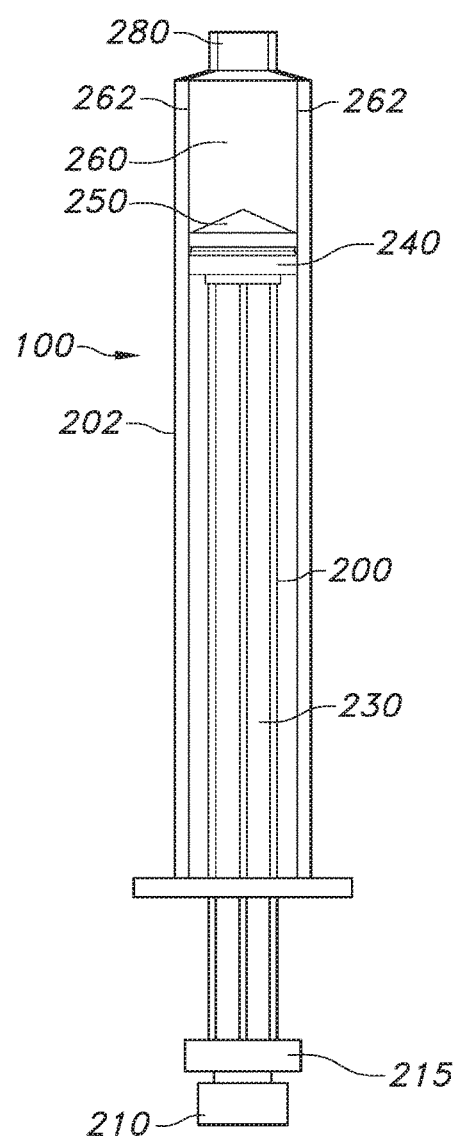
FIG. 1 shows a perspective front view of an exemplary embodiment of the cannulated dose delivery device.

One of the objectives of the current technology is to provide a complete delivery of agents to a subject, such as a patient, by flushing the syringe, without compromising the sterility of the injection. Turning to FIG. 1, a cannulated dose delivery device 100 is shown. The cannulated dose delivery device 100 is an assembly of a number of components including a plunger 200 housed in barrel 202. The plunger 200 is configured to connect to a syringe (not shown) via a plunger proximal end connector 210, to receive a washing agent. The cannulated dose delivery device 100 includes a plunger end cap 250. The plunger end cap 250 is configured to facilitate washing the walls 262 of the drug or agent delivery chamber 260 to provide a more complete dose into the patient's intravenous connection. The cannulated dose delivery device 100 is configured to connect to a patient delivery port 340 (FIG. 6) such as a patient's IV connector through a distal end connector 280.

Figure 2:
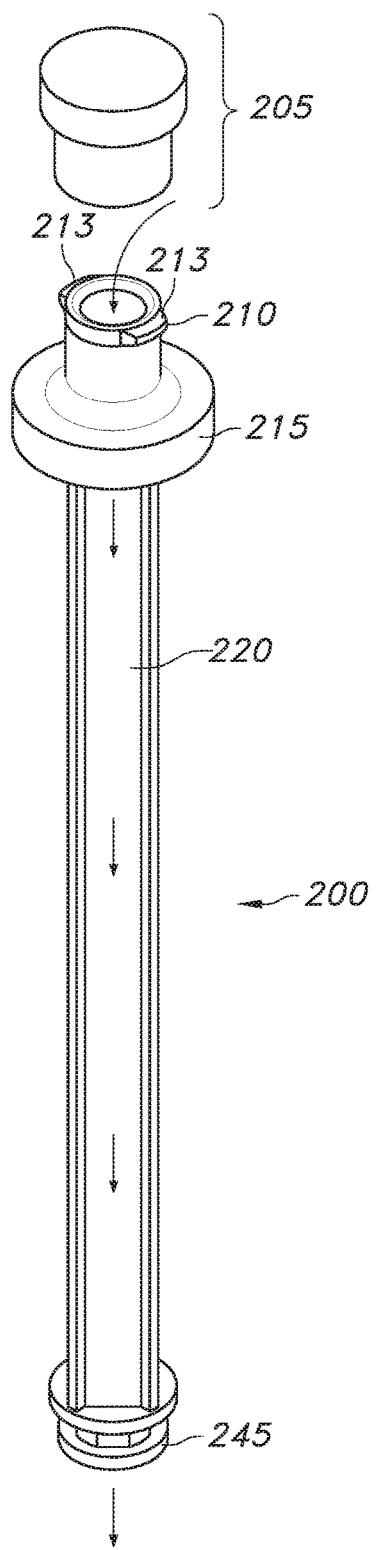
FIG. 2 shows a perspective rear view of a portion of an exemplary embodiment of the cannulated dose delivery device
Figure 3A:
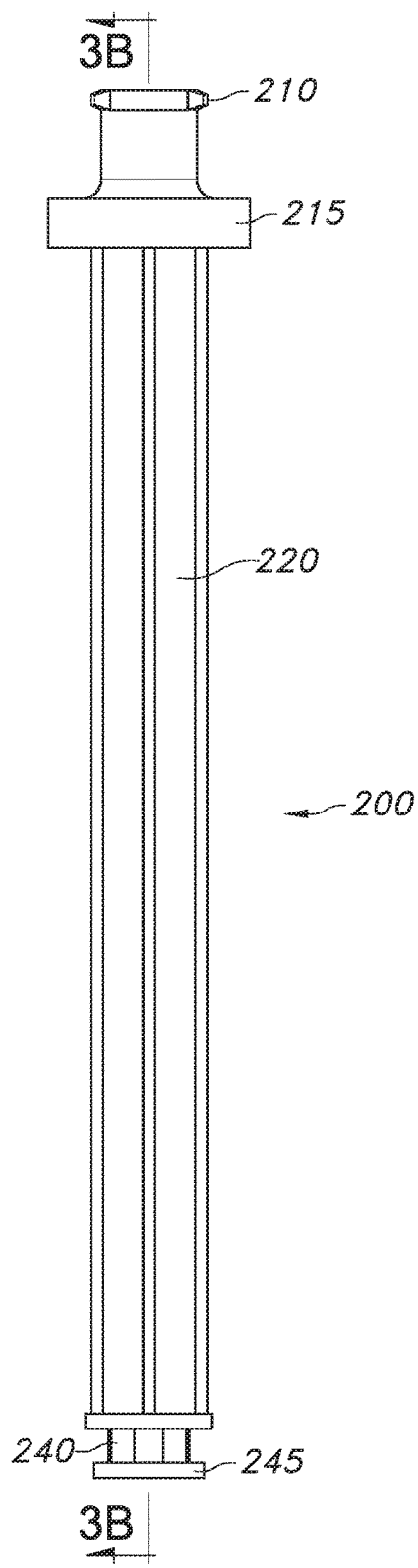
FIGS. 3A and 3B shows a sectional view at A-A of an exemplary embodiment of a portion of the cannulated dose delivery device.
Figure 3B:
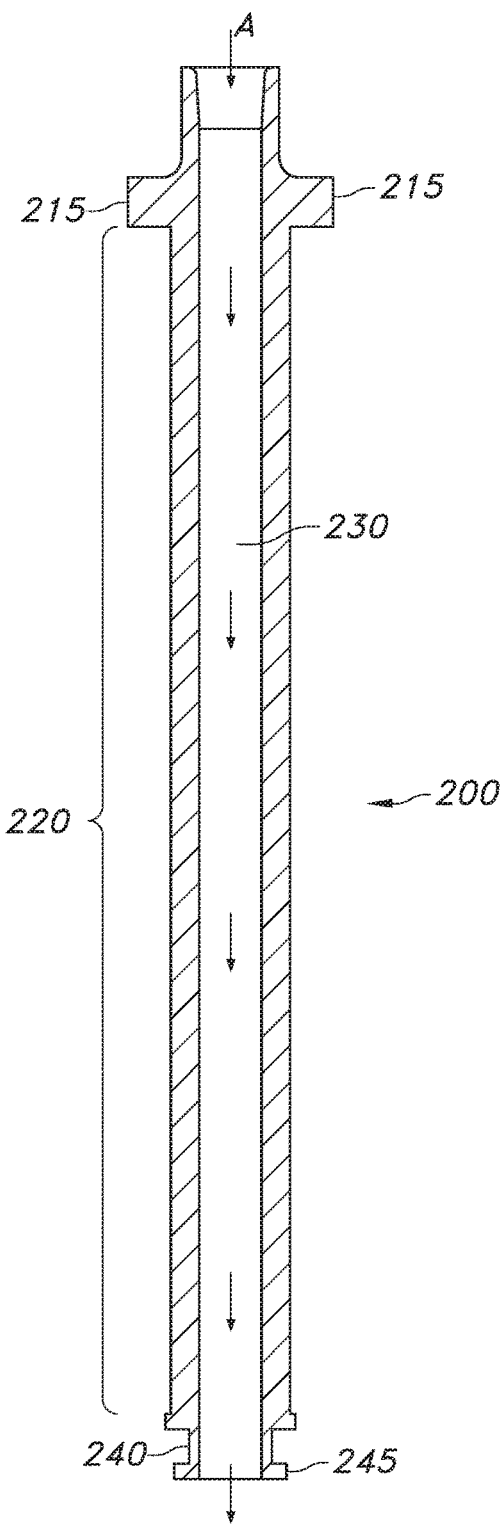

Now referring to FIGS. 2, 3A, and 3B, in this exemplary embodiment, a plunger 200 subassembly is shown. The plunger 200 includes a plunger top cap 205. The plunger top cap 205 is configured to fit on and seal the plunger proximal end connector 210. In the exemplary embodiment, the plunger proximal end connector 210 is a luer-lock. A luer-lock is a dose connection that can be easily released, but maintains sterility of the connection between devices. The main feature of a luer-lock is a bayonet lock, a tapered joint and when connected is leak tight, but easily separated by hand. A typical luer-lock includes two bayonet projections 213 to allow a plunger top cap 205 to be twisted on, pulling the tapered joint tight and preventing accidental separation of the components. When the plunger top cap 205 is removed, the plunger proximal end connector 210 is configured to be attached a saline syringe (not shown) for flushing of a dosing chamber. A flange 215 is provided to facilitate the manipulation of the plunger 200, to aid in providing a dose to the patient.

The middle section 220 of the cannulated dose delivery device 100 forms an elongated barrel and includes an internal chamber 230 sized to allow the flow of liquid through the plunger end cap 250. For nuclear medicine applications, the diameter of the internal chamber 230 varies based on type of injection being provided to the patient. The internal chamber 230 connects to the plunger proximal end connector 210 and to the distal plunger connector 240 to define a fluid pathway in cannulated dose delivery device 100.

The distal end of the plunger 200 of the cannulated dose delivery device 100 includes a distal plunger connector 240 having a retaining member 245. The retaining member 245 projects from the distal plunger connector 240 and forms a generally "T" shaped retaining member in an exemplary embodiment. This portion of the cannulated dose delivery device 100 can be constructed of a biocompatible, pharmacologically inert sterilizeable clear plastic, such as, polyvinyl chloride, high-density polyethylene ("HDPE") or polypropylene or the like.

Now referring to FIGS. 4A and 4B, 5A and 5B, a plunger end cap 250 is shown. The plunger end cap 250 includes an external groove 253 that is configured to prevent leakage of fluid agents. The plunger end cap 250, in an exemplary embodiment, is made from a thermoplastic elastomeric or similarly deformable and sterilizable materials. The plunger end cap 250 provides two functions: it facilitates the fluid connection to the internal chamber 230 and is sized to allow the flow of liquid through the cannulated dose delivery device 100 and the plunger end cap 250 is configured to facilitate washing the walls 262 of the drug or agent delivery chamber 260 to provide a more complete dose into the patient's intravenous connection.

Now referring to FIGS. 5A and 5B, this exemplary embodiment, a section of the thermoplastic elastomeric plunger end cap 250 is peeled back or deformed to allow the plunger retaining member 245, to be inserted into a conforming receiving section 255 in the proximal end 254 of the plunger end cap 250 to form the fluid resistant seal.

Figure 4A:
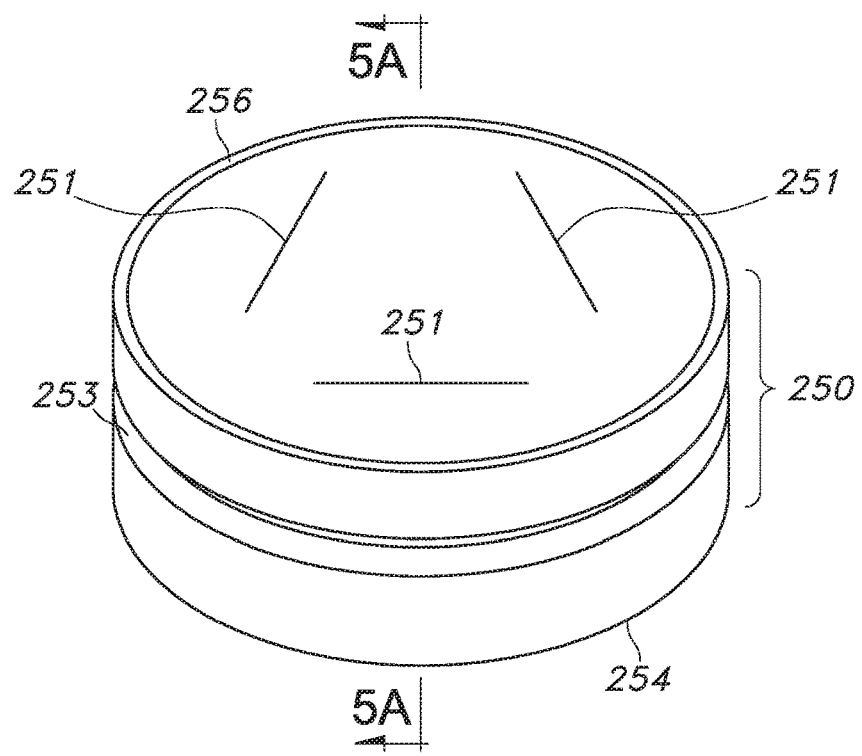
FIG. 4A and 4B show exemplary embodiments of the plunger end cap of the cannulated dose delivery device.
Figure 4B:
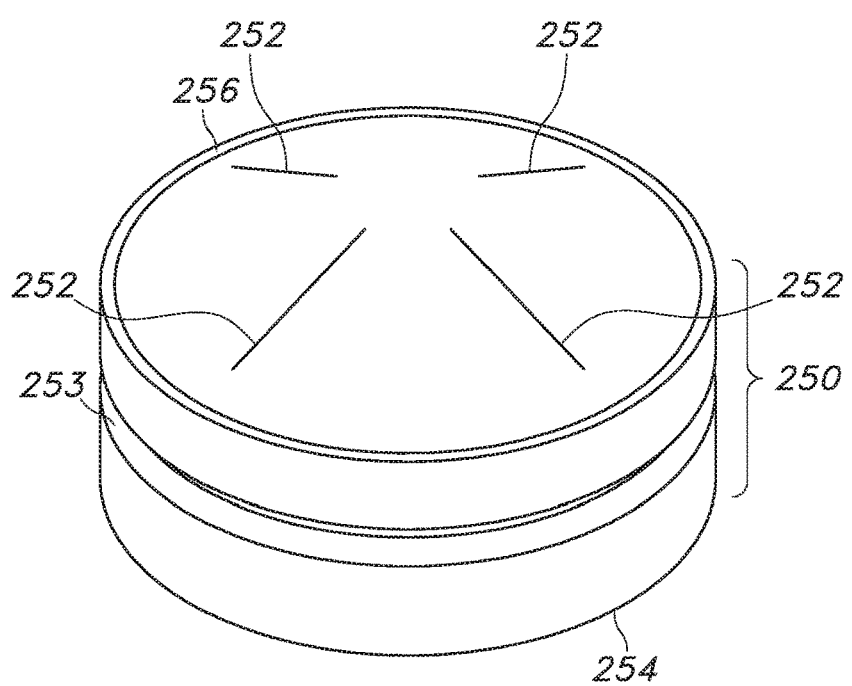

Now referring to FIGS. 4A and 4B exemplary embodiments of the plunger end cap 250 of the cannulated dose delivery device 100 are shown. In embodiment, 4A, the plunger end cap 250 includes a plurality of horizontal slits 251 in the distal end 256 projecting away from the cannulated dose delivery device 100. The plurality of horizontal slits 251 in the plunger end cap 250 are to a moderate extent parallel with the distal end 256 and can be either straight or curved, The function of these horizontal slits 251 is to wash the walls 262 of a drug or agent deliver chamber 260 to provide a more complete dose into the patient's intravenous connection (not shown). In this exemplary embedment, a plurality of horizontal slits 251 are arranged at about 120 degree angles relative to each other. Upon the application of fluid pressure, the horizontally located slits 251 open and direct, the wash upon the walls 262 of the dosing chamber 260. The fluid pressure of wash solution, in particular, the added saline, facilitates the washing of the chamber walls 262 of a dosing chamber 260 to facilitate the internal flushing of a syringe dose chamber 260.

in embodiment 4B the plunger end cap 250 includes a plurality of vertical slits 252 in the distal-end 256 projecting away from the cannulated dose delivery device 100. The plurality of vertical slits 252 of the plunger end cap 250 function to provide a more complete dose into the patient's intravenous connection (not shown). In an exemplary embodiment, plurality of vertical slits 252 do not bisect each other to increase the rigidity of the plunger end cap 250. The plurality of vertical slits 252 of the plunger end cap 250 are to a moderate extent perpendicular with the distal end 256 and can be straight or curved as desired by one skilled in the art.

The terms horizontal slits 251 and vertical slits 252 are intended to cover any equivalent orientation of slits covering the range from perpendicular to parallel that facilitate the internal flushing of a syringe dose chamber 260. The fluid pressure of wash solution, in particular the added saline, facilitates the washing of the chamber walls 262 of a dosing chamber 260.

Now referring to FIG. 6, saline flush syringe 310 is attached to the plunger proximal end connector 210 on the proximal end of the cannulated dose delivery device 100. The saline solution is administered through the middle section 220 of the cannulated dose delivery device 100 that includes an internal chamber 230, which allows flow of the saline solution into the dosing chamber 260 via the plurality of slits 252 in the plunger end cap 250. This allows the walls 262 of the dosing chamber 260 to be rinsed to complete the dose to be delivered while maintaining the sterile dose pathway.

Now referring to FIG. 7, sterilized cannulated dose delivery devices 100 are packaged in a container 350, such as a perforated 352 blister pack, that can be separated to form one sterilized unit 351. The packaged cannulated dose delivery device 100 can be sterilized by gaseous or radiation means known to one skilled in the art, and provide an integral system to flush a dosing chamber 260.

In a medical procedure, one sterilized unit 351 is detached from the package 350 by separating the perforation 251. The sterilized unit 351 is opened to provide the cannulated dose delivery device 100. A needle is attached to the distal end attachment port 280 of the cannulated dose delivery device 100 and a dose of the contrast agent or medication is drawn into the delivery chamber 260. The cannulated dose delivery device distal connector 280 is attached to a patient delivery port 340 such as a patient's IV. The plunger top cap 205 is removed. The saline flush syringe 310 is connected to the cannulated dose delivery device 100 via the plunger proximal connector 210. The saline flush syringe 310 is depressed releasing the wash fluid into the syringe 200. The washing agent flows through the plunger end cap 250 and into the dosing chamber 260. The dosing chamber 260 is rinsed and the patient receives a complete dose of the agent/drug plus the saline, without compromising the sterility of the injection.

While the invention has been described with reference to preferred and example embodiments, it will be understood by those skilled in the art that a variety of modifications, additions and deletions are within the scope of the invention, as defined by the following claims.

I claim:

1. An apparatus comprising:
a plunger housed in a barrel, wherein the plunger comprises;
a plunger proximal end connector configured to receive a washing agent;
a plunger end cap configured to facilitate the washing of a delivery chamber of the barrel;
an elongated cylinder having an internal chamber defining a fluid pathway between the plunger proximal end connector and the plunger end cap; wherein the plunger end cap comprises a plurality of slits in the distal end of the plunger end cap, wherein the slits are spaced apart.

2. The apparatus of claim 1 further comprising a distal connector configured to connect the apparatus to a delivery port.

3. The apparatus of claim 1 wherein the plunger proximal end connector is a luer-lock adaptor.

4. The apparatus of claim 1 wherein the plunger end cap is connected to the plunger by a "T" shaped retaining member.

5. The apparatus of claim 1 wherein of each of the plurality of slits in the plunger end cap are parallel with a distal end of the plunger end cap.

6. The apparatus of claim 5 wherein the plurality of slits are at a 120 degree angle relative to each other.

7. The apparatus of claim 1 wherein each of the plurality of slits in the plunger end cap are perpendicular with a distal end of the plunger end cap.

8. The apparatus of claim 1 wherein the plunger end cap further comprises an internal groove and an external groove.

9. The apparatus of claim 8 wherein the internal groove comprises a conforming receiving section in the distal proximal end of the plunger end cap to accept the plunger retaining member to form a fluid resistant seal.

10. The apparatus of claim 1 sterilized and packaged in a container.

11. The apparatus of claim 1 further comprising a plunger top cap.

12. A cannulated dose delivery system comprising:
a plunger housed in a barrel, wherein the plunger comprises: a plunger proximal end connector configured to receive a washing agent; a plunger end cap configured to facilitate the washing of a delivery chamber of the barrel; an elongated cylinder having an internal chamber defining a fluid pathway between the plunger proximal end connector and the plunger end cap; wherein the plunger end cap comprises a plurality of slits in the distal end of the plunger end cap wherein the slits are spaced apart; a distal connector configured to connect the plunger housing to a delivery port; and;
a saline flush syringe connected to the plunger proximal end connector.

13. The cannulated dose delivery system of claim 12, further comprising a delivery port to a patient.

14. The cannulated dose delivery system of claim 12 wherein each of the plurality of slits in the plunger end cap are parallel with a distal end of the plunger end cap.

15. The cannulated dose delivery system of claim 14 wherein the plurality of slits are at a 120 degree angle relative to each other.

16. The cannulated dose delivery system of claim 14 wherein each of the plurality of slits in the plunger end cap are perpendicular with a distal end of the plunger end cap.

17. A method to increase dosage delivery to a patient while maintaining a sterile fluid pathway comprising:
providing a plunger housed in a barrel, wherein the plunger comprises: a plunger proximal end connector configured to receive a washing agent; a plunger end cap configured to facilitate the washing of a delivery chamber of the barrel; an elongated cylinder having an internal chamber defining a fluid pathway between the plunger proximal end connector and the plunger end cap; wherein the plunger end cap comprises a plurality of slits in the distal end of the plunger end cap wherein the slits are spaced apart; a distal connector configured to connect a cannulated dose delivery device to a delivery port and a plunger top cap;
attaching a needle to the distal end attachment port;
connecting a saline flush syringe to the plunger proximal end connector;
connecting a delivery port to a patient;
delivering a dose of the contrast agent or medication to the delivery chamber;
attaching the cannulated dose delivery device distal connector to a patient delivery port;
removing the plunger top cap;

connecting the saline flush syringe to the cannulated dose delivery device via the plunger proximal connector; and depressing the flush syringe to deliver a washing solution to the dosing chamber to increase dosage delivery to a patient.

18. The method of claim 17 wherein the wash solution is saline.

* * * * *